United States Patent
He et al.

(10) Patent No.: US 10,675,462 B2
(45) Date of Patent: Jun. 9, 2020

(54) MEDICAL DEVICE AND RELATED METHODS

(71) Applicant: Boston Scientific Scimed, Inc., Maple Grove, MN (US)

(72) Inventors: Ding Sheng He, Tyngsboro, MA (US); Sandra Nagale, Bolton, MA (US); Allan Charles Shuros, St. Paul, MN (US); Charles Gibson, Malden, MA (US); Lynne Swanson, Edina, MN (US); Dennis Werner, Big Lake, MN (US); Timothy Paul Harrah, Cambridge, MA (US); Mark Boden, Harrisville, RI (US); Michael Charles Peterson, Newburyport, MA (US); Steven Diamond, Tewksbury, MA (US); Amedeo Chiavetta, Derry, NH (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 270 days.

(21) Appl. No.: 15/342,785

(22) Filed: Nov. 3, 2016

(65) Prior Publication Data

US 2017/0120048 A1 May 4, 2017

Related U.S. Application Data

(60) Provisional application No. 62/250,585, filed on Nov. 4, 2015.

(51) Int. Cl.
*A61N 1/36* (2006.01)
*A61B 5/0488* (2006.01)
(Continued)

(52) U.S. Cl.
CPC ........ *A61N 1/36007* (2013.01); *A61B 5/0492* (2013.01); *A61B 5/04882* (2013.01);
(Continued)

(58) Field of Classification Search
CPC ................................................. A61B 5/04884
See application file for complete search history.

(56) References Cited

U.S. PATENT DOCUMENTS

| | | |
|---|---|---|
| 5,127,077 A | 6/1992 | Iyer et al. |
| 5,156,151 A | 10/1992 | Imran |
| 5,261,889 A | 11/1993 | Laine et al. |
| 5,277,201 A | 1/1994 | Stern |
| 5,293,869 A | 3/1994 | Edwards et al. |
| 5,309,910 A | 5/1994 | Edwards et al. |

(Continued)

FOREIGN PATENT DOCUMENTS

| | | |
|---|---|---|
| WO | WO 2015/067791 | 7/2005 |
| WO | WO 2012/083155 A2 | 6/2012 |

(Continued)

OTHER PUBLICATIONS

International Search Report and Written Opinion dated May 12, 2017, in International App. No. PCT/US2016/060366 (12 pages).

(Continued)

*Primary Examiner* — Carl H Layno
*Assistant Examiner* — Jennifer L. Ghand
(74) *Attorney, Agent, or Firm* — Bookoff McAndrews, PLLC (57) ABSTRACT

In one aspect, the present disclosure is directed to a method for identifying a site with a patient for treatment. The method may include engaging a plurality electrodes with an interior wall of the patient at a plurality of locations. The method may also generating a virtual map of a plurality of electrodes, wherein each of the plurality of electrodes is displayed with a first indicia. The method may also include displaying each of the plurality of electrodes engaged with the interior wall with a second indicia, measuring electrical activity, identifying at least one site for treatment based on the measured resulting electrical activity, and displaying each of the plurality of electrodes identified for treatment with a third indicia.

17 Claims, 5 Drawing Sheets

(51) Int. Cl.
*A61B 5/053* (2006.01)
*A61B 5/00* (2006.01)
*A61B 5/0492* (2006.01)
*A61B 5/20* (2006.01)
*A61B 18/14* (2006.01)
*A61N 1/02* (2006.01)
*A61N 1/30* (2006.01)
*A61B 17/32* (2006.01)
*A61B 18/02* (2006.01)
*A61B 18/00* (2006.01)

(52) U.S. Cl.
CPC ........ *A61B 5/04884* (2013.01); *A61B 5/0536* (2013.01); *A61B 5/0538* (2013.01); *A61B 5/202* (2013.01); *A61B 5/4836* (2013.01); *A61B 18/1492* (2013.01); *A61N 1/025* (2013.01); *A61N 1/303* (2013.01); *A61B 18/02* (2013.01); *A61B 2017/320069* (2017.08); *A61B 2018/0016* (2013.01); *A61B 2018/00029* (2013.01); *A61B 2018/00267* (2013.01); *A61B 2018/00517* (2013.01); *A61B 2018/00577* (2013.01); *A61B 2018/00839* (2013.01); *A61B 2018/00875* (2013.01); *A61B 2018/1465* (2013.01); *A61B 2018/1475* (2013.01)

(56) References Cited

U.S. PATENT DOCUMENTS

| | | |
|---|---|---|
| 5,313,943 A | 5/1994 | Houser et al. |
| 5,324,284 A | 6/1994 | Imran |
| 5,345,936 A | 9/1994 | Pomeranz |
| 5,348,554 A | 9/1994 | Imran et al. |
| 5,366,490 A | 11/1994 | Edwards et al. |
| 5,370,675 A | 12/1994 | Edwards et al. |
| 5,435,805 A | 7/1995 | Edwards et al. |
| 5,471,982 A | 12/1995 | Edwards et al. |
| 5,486,161 A | 1/1996 | Lax et al. |
| 5,494,042 A | 2/1996 | Panescu et al. |
| 5,545,171 A | 8/1996 | Sharkey et al. |
| 5,545,193 A | 8/1996 | Fleischman et al. |
| 5,588,960 A | 12/1996 | Edwards et al. |
| 5,617,876 A | 4/1997 | van Duyl |
| 5,636,634 A | 6/1997 | Kordis et al. |
| 5,662,108 A | 9/1997 | Budd et al. |
| 5,704,353 A | 1/1998 | Kalb et al. |
| 5,706,809 A | 1/1998 | Littmann et al. |
| RE35,880 E | 8/1998 | Waldman et al. |
| 5,836,874 A | 11/1998 | Swanson et al. |
| 5,849,011 A | 12/1998 | Jones et al. |
| 5,860,974 A | 1/1999 | Abele |
| 5,893,885 A | 4/1999 | Webster, Jr. |
| 5,961,513 A | 10/1999 | Swanson et al. |
| 5,964,796 A | 10/1999 | Imran |
| 6,006,755 A | 12/1999 | Edwards |
| 6,009,877 A | 1/2000 | Edwards |
| 6,014,579 A | 1/2000 | Pomeranz et al. |
| 6,038,472 A | 3/2000 | Williams et al. |
| 6,056,744 A | 5/2000 | Edwards |
| 6,073,052 A | 6/2000 | Zelickson et al. |
| 6,088,610 A | 7/2000 | Littman et al. |
| 6,115,626 A | 9/2000 | Whayne et al. |
| 6,156,029 A | 12/2000 | Mueller |
| 6,273,886 B1 * | 8/2001 | Edwards ............... A61B 18/12 606/34 |
| 6,296,608 B1 | 10/2001 | Daniels et al. |
| 6,416,505 B1 | 7/2002 | Fleischman |
| 6,463,331 B1 | 10/2002 | Edwards |
| 6,571,127 B1 | 5/2003 | Ben-Haim et al. |
| 6,645,201 B1 | 11/2003 | Utley et al. |
| 6,660,003 B1 | 12/2003 | DeVore et al. |
| 6,673,070 B2 | 1/2004 | Edwards |
| 6,692,490 B1 | 2/2004 | Edwards |
| 6,994,704 B2 | 2/2006 | Qin et al. |
| 7,022,105 B1 | 4/2006 | Edwards |
| 7,056,320 B2 | 6/2006 | Utley et al. |
| 7,125,407 B2 | 10/2006 | Edwards et al. |
| 7,165,551 B2 | 1/2007 | Edwards et al. |
| 7,326,235 B2 | 2/2008 | Edwards et al. |
| 7,483,734 B2 * | 1/2009 | Colthurst ............... A61B 5/0531 600/547 |
| 7,615,014 B2 | 11/2009 | Omata et al. |
| 7,648,500 B2 | 1/2010 | Edwards et al. |
| 7,742,795 B2 | 6/2010 | Stone et al. |
| 7,850,685 B2 | 12/2010 | Kunis et al. |
| 8,177,781 B2 | 5/2012 | Thomas et al. |
| 8,672,923 B2 | 3/2014 | Ladtkow et al. |
| 9,687,167 B2 * | 6/2017 | Laughner ............... A61B 5/0452 |
| 2001/0009976 A1 | 7/2001 | Panescu et al. |
| 2002/0013581 A1 | 1/2002 | Edwards et al. |
| 2002/0026188 A1 | 2/2002 | Balbierz et al. |
| 2002/0072742 A1 | 6/2002 | Schaefer et al. |
| 2003/0055307 A1 | 3/2003 | Elmaleh et al. |
| 2003/0171645 A1 | 9/2003 | Silverman et al. |
| 2003/0212394 A1 | 11/2003 | Pearson et al. |
| 2003/0220636 A1 * | 11/2003 | Bowman ............... A61B 18/1492 606/28 |
| 2004/0068203 A1 | 4/2004 | Gellman |
| 2004/0153058 A1 | 8/2004 | West et al. |
| 2004/0176755 A1 | 9/2004 | Lafontaine |
| 2004/0186468 A1 | 9/2004 | Edwards |
| 2006/0190022 A1 | 8/2006 | Beyar et al. |
| 2006/0173359 A1 | 9/2006 | Lin et al. |
| 2006/0247026 A1 | 11/2006 | Starkebaum |
| 2007/0282184 A1 | 12/2007 | Roberts |
| 2008/0009747 A1 | 1/2008 | Saadat et al. |
| 2008/0015569 A1 | 1/2008 | Saadat et al. |
| 2008/0125709 A1 | 5/2008 | Chang et al. |
| 2008/0215040 A1 | 9/2008 | Paithankar et al. |
| 2009/0012469 A1 | 1/2009 | Nita |
| 2010/0152704 A1 | 6/2010 | Lee et al. |
| 2010/0166739 A1 | 7/2010 | Chancellor et al. |
| 2010/0198139 A1 | 8/2010 | Glickman |
| 2010/0256594 A1 | 10/2010 | Kimmell et al. |
| 2010/0268191 A1 | 10/2010 | Trudel et al. |
| 2011/0093030 A1 * | 4/2011 | Goetz ............... A61N 1/0553 607/17 |
| 2011/0166516 A1 | 7/2011 | Orr |
| 2012/0265198 A1 | 10/2012 | Crow et al. |
| 2013/0018281 A1 | 1/2013 | Nagale et al. |
| 2013/0035576 A1 | 2/2013 | O'Grady et al. |
| 2013/0053916 A1 | 2/2013 | Sambelashvili et al. |
| 2013/0072855 A1 | 3/2013 | Sherry et al. |
| 2013/0090640 A1 | 4/2013 | Nagale et al. |
| 2013/0090648 A1 | 4/2013 | Nagale et al. |
| 2014/0039356 A1 | 2/2014 | Sachs et al. |
| 2014/0081257 A1 | 3/2014 | Ghoneim |
| 2014/0148798 A1 | 5/2014 | Sachs et al. |
| 2014/0257268 A1 | 9/2014 | Sachs et al. |
| 2014/0276590 A1 | 9/2014 | Hiller et al. |
| 2014/0276593 A1 | 9/2014 | Nagale et al. |
| 2014/0343629 A1 * | 11/2014 | Kaula ............... A61N 1/37247 607/59 |
| 2015/0011843 A1 | 1/2015 | Toth et al. |
| 2016/0278660 A1 | 9/2016 | Nagale et al. |

FOREIGN PATENT DOCUMENTS

| | | |
|---|---|---|
| WO | WO 2013/039711 A2 | 3/2013 |
| WO | WO 2013/160772 A2 | 10/2013 |
| WO | 2013/173917 A1 | 11/2013 |
| WO | WO 2013/188640 A1 | 12/2013 |

OTHER PUBLICATIONS

T. Hague et al., "The effect of heating (37-41 degrees C)on detrusor contractile function in rabbit mucosa-intact and denuded preparations," Neurology and Urodynamics, Beijing, People R. China: 42$^{nd}$ Annual Meeting of International Continence Society (ICS) vol. 31 (6), pp. 1027-1028.

(56) References Cited

OTHER PUBLICATIONS

T. Hague et al., "ICS 2012 Abstract Form, 42$^{nd}$ Annual Meeting of the International Continence Society, Oct. 15-19, 2012, Beijing China," 2 pages.
Partial International Search Report issued in PCT/US2012/059028, dated Jan. 23, 2013, 2 pages.
"Core Technology," retrieved from Contura website at http://www.contura.com/produsts/core-technology on Dec. 28, 2012 (2 pages).
Hillel, Alexander T. et al., "Photoactivated Composite Biomaterial for Soft Tissue Restoration in Rodents and in Humans," Science Translation Medicine, vol. 3, Iss. 93, p. 93ra67 (2011) (13 pages).
Karajanagi, Sandeep S. et al., "Assessment of Canine Vocal Fold Function After Injection of a New Biomaterial Designed to Treat Phonatory Mucosal Scarring," Annals of Otology, Rhinology & Laryngology, vol. 120, pp. 175-184 (2011), Abstract (1 page).
"Products: Tissue Repair," retrieved from Fidia website at http://www.fidlapharma.com/files/index.cfm?id_rst=137 on Dec. 28, 2012 (3 pages).
"Treatment of morbid obesity by intraparietogastric administration of botulinum toxin: a randomized, double-blind, controlled study" Internationl Journal of Obesity (2007) 31, 707-712 (6 pages).
"Alerations of Gastrointestinal Motility in Obesity" Obesity Research vol. 12 No. 11 Nov. 2004 1723-1732 (10 pages).
Gulur, et al., "Management of Overactive Bladder," Nature Reviews/Urology, Oct. 2010, vol. 7, pp. 572-582.
Gillespie, et al., "On the Origins of the Sensory Output from the Bladder: the Concept of Afferent Noise," BJU International, 2009, vol. 103, pp. 1324-1333.
Steers, William D., "Pathophysiology of Overactive Bladder and Urge Urinary Incontinence," Reviews in Urology, 2002, vol. 4, Suppl. 4, pp. S7-S18.
Charlton et al., "Focal changes in nerve, muscle and connective tissue in normal and unstable human bladder," BJU International, 1999, pp. 953-960, 84.
Drake et al., Model of peripheral autonomous modules and a myovesical plexus in normal and overactive bladder function, The Lancet, 2001, pp. 401-403, 358.
Mustafa et al., "Cooling-induced bladder contraction: studies on isolated detrusor muscle preparations in the rat," *Urology*, 1999, pp. 653-657, 53.
Roosen et al., "Characteristics of spontaneous activity in the bladder trigone," *European Urology*, 2009, pp. 346-354, 56.
Lemke et al., "Multisensor array for pH, $K^+$, $Na^+$ and $Ca^{2+}$ measurements based on coated-film electrodes," Sensors and Actuators B, 1992, pp. 488-491, 7.
Kuo et al., "Novel Biomarkers for Diagnosis and Therapeutic Assessment of Overactive Bladder: Urinary Nerve Growth Factor and Detrusor Wall Thickness," LUTS, 2009, pp. 559-561, 1.
International Search Report and Written Opinion for International Application No. PCT/US2016/023881, dated Jun. 29, 2016 (16 pages).

* cited by examiner

MEDICAL DEVICE AND RELATED METHODS

CROSS-REFERENCE TO RELATED APPLICATIONS

This patent application claims the benefit of priority under 35 U.S.C. § 119 to U.S. Provisional Patent Application No. 62/250,585, filed Nov. 4, 2015, which is herein incorporated by reference in its entirety.

FIELD OF THE DISCLOSURE

The disclosure relates generally to utilizing electrodes as diagnostic and treatment tools, and, more specifically, to methods and associated systems for identifying sites within a patient to apply treatment.

BACKGROUND

Portions of the human body sometimes fail to function properly. Often the cause of the malfunction is limited to a specific area or location, and not the entire malfunctioning portion (e.g., an entire organ, an entire body tract, etc.). It can be unnecessary, wasteful, or even dangerous to treat the entire organ, tract, etc., because healthy and/or properly functioning areas will be treated too. For example, a patient's digestive tract may not be functioning properly, but the cause may only be a small portion of the small intestine. Treating the entire digestive tract, including properly functioning portions, may cause the properly functioning portions (e.g., the entire digestive tract except the small portion of the small intestine) to function improperly. In another example, only certain portions of the bladder may cause an overactive bladder condition, and thus only those portions may require treatment.

Overactive Bladder or OAB is one of the factors that can result in urinary incontinence conditions. OAB is a chronic urological condition characterized broadly as the involuntary and uncontrollable urge felt by a subject to relieve the bladder, leading to abnormally high urinating frequency. Such conditions may occur due to frequent and spontaneous contractions of the detrusor muscle of the pelvic region of a subject.

Overactive bladders often exhibit localized changes in detrusor morphology, likely originating from defects on cellular and multicellular level. Such cell related deviations may be attributed to local pathological changes in the muscle condition or topology that may contribute to anomalies in the functionality of the detrusor muscle on a macroscopic scale. These changes are correlated to the observed local pathological changes in the muscle (e.g. patchy denervation, increased amount of connective tissue between muscle bundles) which may contribute to abnormal function of the detrusor muscle on a macroscopic scale. Moreover, some studies suggest that abnormal activity may originate from one or more distinct anatomical areas of the bladder such as the dome, internal sphincter, or the trigone.

Current solutions for overactive bladder treatment (e.g. systemic drugs, nerve stimulation, and Botox injections) target the abnormal function of the entire bladder and may not specifically address local and anatomical abnormalities, thereby indicating a need for methods and devices capable of identifying and providing therapy to specific areas where local bladder abnormality originates. In addition, current treatments, like Botox injections, need to be repeated as the effect wears off over time. Further, overtreatment with Botox leads to urinary retention which requires self-catheterization in order to void. Similarly, solutions that fail to identify the location of the abnormalities or treat only these specific locations may prolong the therapeutic effect and increase procedure time. As such, existing solutions for OAB may fail to properly address local and anatomical abnormalities of the detrusor muscle, thereby indicating the need for alternative therapies for local bladder abnormalities.

The devices and methods of the current disclosure may rectify some of the deficiencies described above or other deficiencies in the art.

SUMMARY

Aspects of the present disclosure provide methods for identifying a treatment site.

It is to be understood that both the foregoing general description and the following detailed description are exemplary and explanatory only and are not restrictive.

In one example, a treatment system may include a plurality of electrodes, a display, a memory device configured to store instructions for evaluating electrical signals, and a processor configured to execute the instructions to perform a method. The method performed by the processor may include communicating to the display a virtual map including a representative marking with a first indicia for each of the plurality of electrodes, determining which of the plurality of electrodes are in contact with internal tissue, communicating to the display the representative marking with a second indicia for each of the plurality of electrodes determined to be in contact with internal tissue, measuring electrical activity at each of the plurality of electrodes in contact with internal tissue, determining at least one of the plurality of electrodes for treatment based on the measured electrical activity, and communicating to the display the representative marking for the at least one of the plurality of electrodes for treatment as a third indicia.

Examples of the device may additionally and/or alternatively include one or more other features. For example, the method may include receiving, from the display, a selection of at least one of the plurality of electrodes to apply treatment. The method may further include instructing the treatment system to apply treatment to the tissue in contact with the least one of the plurality of electrodes for treatment. The treatment may include at least one of radio frequency energy, ultrasound energy, laser energy, cryoablation, microwave ablation, a Botox injection, a neurolytic agent, optical energy, irreversible electroporation, magnetics, ultrasound thermal treatment, hydrogel injection, injection of a material to create a physical or chemical barrier for signal transduction, or injection of any drug or drug-carrier combination formulation. Measuring electrical activity may include at least one of measuring spontaneous electrical activity, measuring the results of pacing the plurality of electrodes, or measuring vector impedance. The method may further include after instructing the treatment system to apply treatment to the tissue, measuring electrical activity at each of the plurality of electrodes in contact with tissue. The method may further include determining at least one of the treated plurality of electrodes for no treatment. The method may further include communicating to the display the representative marking for the at least one treated plurality of electrodes as a fourth indicia. The method may include determining at least one of the treated plurality of electrodes for treatment and instructing the treatment system to apply treatment to the tissue in contact with the least one of the treated plurality of electrodes for treatment. The first indicia, second indicia, third indicia, and fourth indicia may be four different colors or shadings. The method may include generating a graphical representation of the measured electrical activity at each of the plurality of electrodes in contact with internal tissue. The method may further include communicating to the display the measured electrical activity at each of the plurality of electrodes in contact with internal tissue. The plurality of electrodes may be disposed on a plurality of legs. The method may further include identifying a leg of the plurality of legs including at least two of the plurality of electrodes determined for treatment. The method may include instructing the treatment system to apply treatment to the tissue in contact with each electrode disposed on the identified leg.

In another example, a method may include generating a virtual map of a plurality of electrodes, wherein each of the plurality of electrodes is displayed with a first indicia, engaging one or more of a plurality of electrodes with an interior wall of the patient at a plurality of locations, displaying each of the plurality of electrodes engaged with the interior wall with a second indicia, measuring electrical activity, identifying at least one site for treatment based on the measured resulting electrical activity, and displaying each of the plurality of electrodes identified for treatment with a third indicia.

Examples of the method may additionally and/or alternatively include one or more other features. For example, the method may further include selecting at least one of the plurality of electrodes for treatment, and applying treatment to the selected plurality of electrodes. The method may further including after applying treatment, measuring electrical activity.

In another example, a method may include engaging one or more of a plurality of electrodes with an interior wall of the patient at a plurality of locations, measuring electrical activity a first time, identifying at least one site for treatment based on the first measured resulting electrical activity, selecting at least one of the identified plurality of electrodes for treatment, applying treatment to the selected the plurality of electrodes, and after applying treatment, measuring electrical activity a second time.

Examples of the method may additionally and/or alternatively include one or more other features. For example, after measuring electrical activity the second time, the method may include determining at least one site for treatment based on the second measured resulting electrical activity.

Additional objects and advantages of the instant disclosure will be set forth in part in the description, which follows, and in part will be obvious from the description, or may be learned by practice of the present disclosure. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the present disclosure and together with the description, serve to explain principles of the disclosure.

DESCRIPTION OF EXEMPLARY EMBODIMENTS

Reference is now made in detail to examples of the present disclosure, examples of which are illustrated in the accompanying drawings. Wherever possible, the same reference numbers will be used throughout the drawings to refer to the same or like parts. The term "distal" refers to a position farther away from a user end of the device. The term "proximal" refers a position closer to the user end of the device. As used herein, the terms "approximately" and "substantially" indicate a range of values within +/−5% of a stated value.

Although examples referring to the bladder and OAB are described here, this disclosure is not limited thereto. The device and methods described herein may be applied to the interior of any hollow organ or the exterior of a hollow organ or other organs/surfaces in the body where electrical activity exists.

The present disclosure relates generally to identifying target sites for treatment of various medical conditions. Specifically, the disclosure relates to inserting an electrode array and contacting multiples sites on an interior wall of a patient. Electrical activity at these sites may then be measured in any way. In particular, as disclosed herein, a device may measure (1) spontaneous electrical activity, (2) vector impedance, and/or (3) resulting activity from paced electrode pairs. The measured electrical activity may be used to identify target site(s) for treatment. In some implementations, therapy may be applied to the target site(s) after identification. The device described herein, including an electrode array, and/or any way of measuring electrical activity may be used to determine whether, and/or to what extent, the applied treatment was effective.

Exemplary Devices

Figure 1:
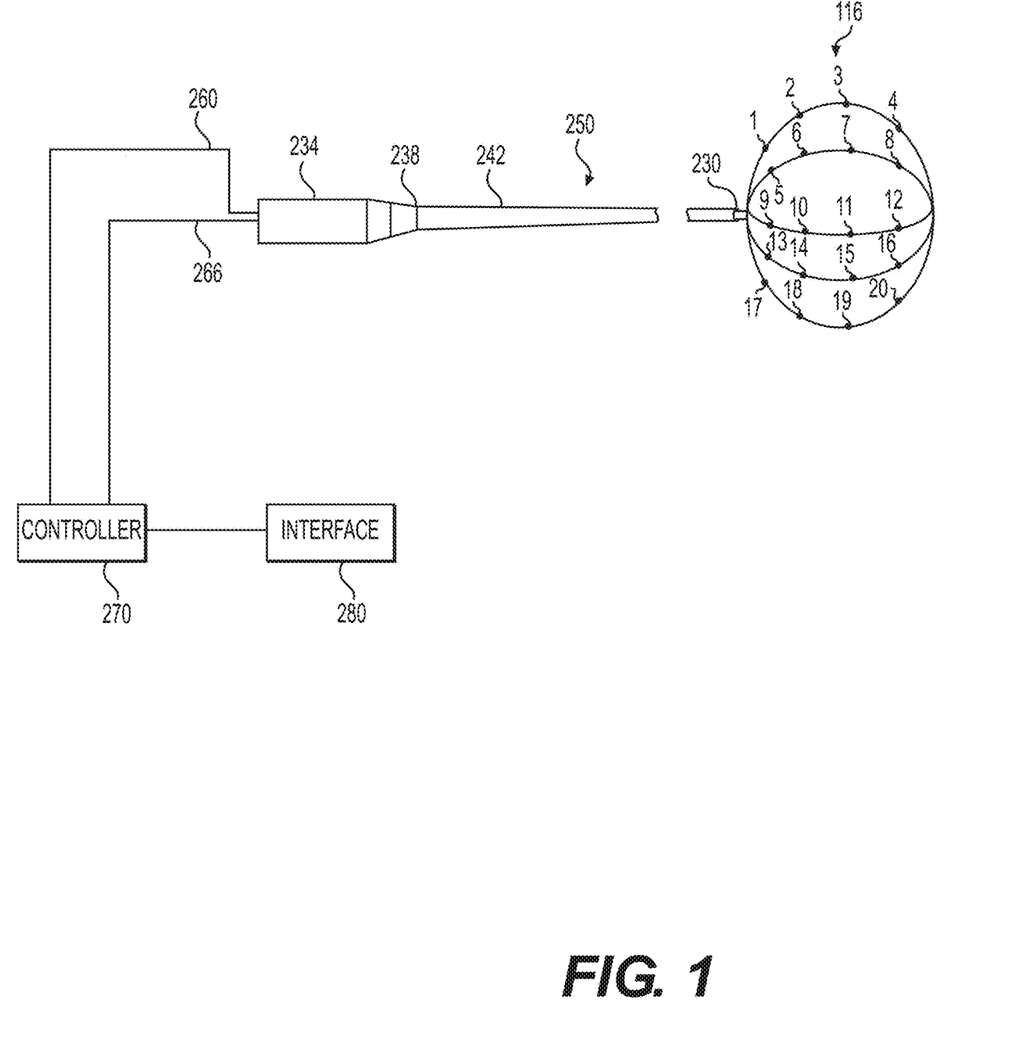
FIG. 1 illustrates a system for identifying sites for treatment and treating a medical condition in accordance with principles of the present disclosure.

FIG. 1 illustrates an exemplary medical device 250. Medical device 250 may be used with any of the methods described herein, including methods of identifying target site(s), providing treatment, and/or determining treatment effectiveness. Other exemplary medical devices and electrode configurations are described in U.S. Provisional Application No. 62/137,979, filed on Mar. 25, 2015; U.S. patent application Ser. No. 13/535,741, filed on Jun. 28, 2012; and U.S. patent application Ser. No. 14/211,440, filed on Mar. 14, 2014, the content of each are herein incorporated by reference.

Medical device 250 of FIG. 1 includes a catheter 242, a handle portion 234, and an electrode array 116. Catheter 242 may have a proximal end 238 and a distal end 230. Handle portion 234 may be disposed at proximal end 238 of catheter 242.

Figure 4:
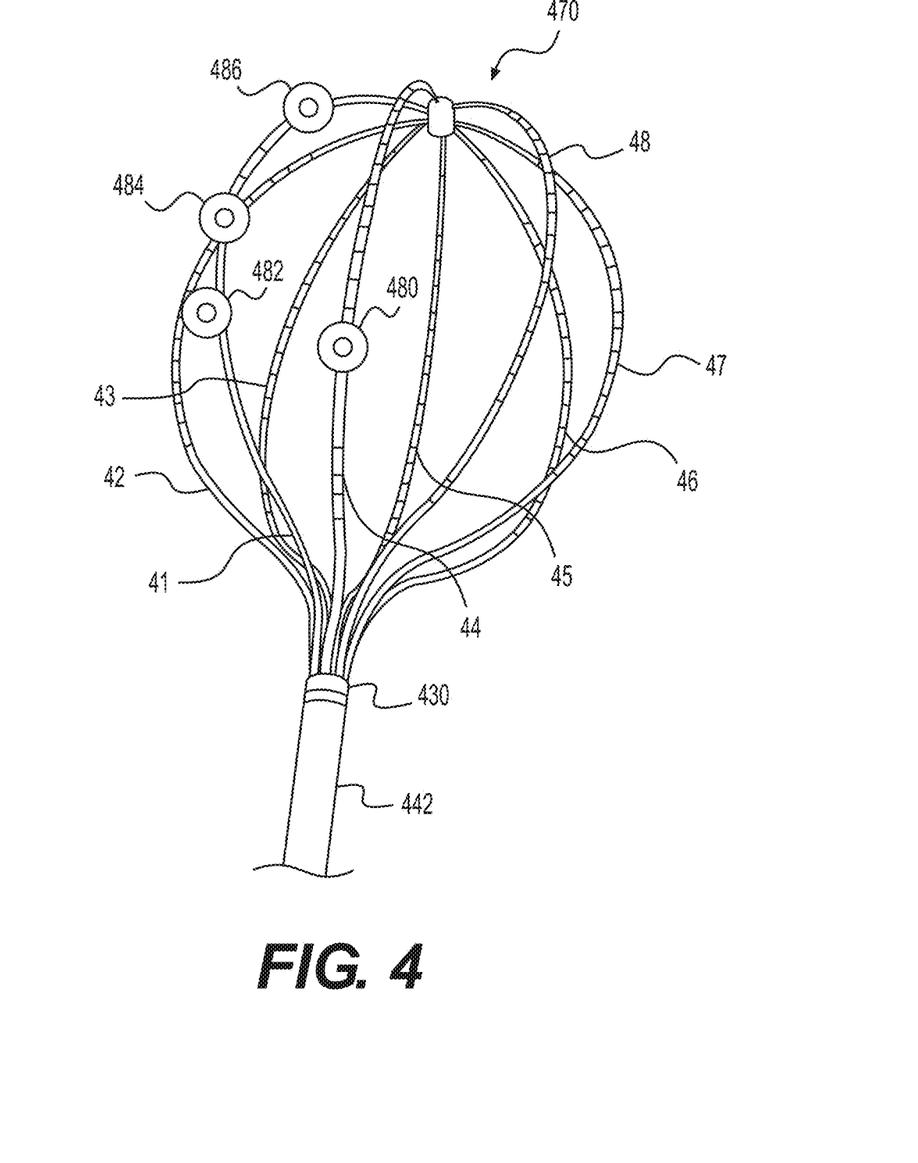
FIG. 4 an exemplary alternative electrode array of the system for identifying sites for treatment in accordance with principles of the present disclosure.

Electrode array 116 may be disposed within catheter 242 or, as shown in FIG. 1, may be deployed out of distal end 230 of catheter 242. Electrode array 116 may be made of, for example, stainless steel, metal-polymer composites, and/or metal alloys of nickel, titanium, copper cobalt, vanadium, chromium, and iron. In one example, the material forming electrode array 116 may be a superelastic material such as nitinol, which is a nickel-titanium alloy. In some examples, expandable arrays may be made of elastic material, including Nitinol. As shown in the example illustrated in FIG. 1, electrode array 116 may include one or more electrodes 1-20 uniformly distributed over electrode array 116 to supply electricity, detect electrical signals, and/or deliver therapeutic treatment to an organ of the patient. Electrodes 1-20 may be capable of measuring electric current or other parameters such as impedance and/or temperature. The same electrodes may be capable of delivering pacing energy. In some examples, medical device 250 may be capable of applying therapy, such as radio-frequency ("RF") energy, ultrasound energy (e.g., high intensity focused ultrasound), laser energy, cryoablation, microwave ablation, Botox injections, neurolytic agents, optical energy sources, irreversible electroporation, magnetics, ultrasound thermal treatment, hydrogel injection, injection of a material to create a physical or chemical barrier for signal transduction, injection of any drug or drug-carrier combination formulation, and/or other suitable technologies that affect the reactivity of nerve(s). Electrode array 116 may include any number of electrodes, in any configuration. Electrode array 116 may include any number of legs (e.g., the leg on which electrodes 1-4 are disposed or the leg on which electrodes 17-20 are disposed), including but not limited to 1-10 legs (e.g., FIG. 1 illustrates an exemplary electrode array with five legs and FIG. 4 illustrates an exemplary electrode array with eight legs). Some or all of the legs may have free distal ends (e.g., the distal end of electrode array 116 may be open). In some examples, the electrode array may alternately be a single lead. The electrode array may be straight when loaded into the catheter. As the electrode array exits the catheter into the bladder, the electrode array may transform (e.g., due to the use of shape-memory material) into a spiral helix that expands to fit the bladder.

Electrodes may be located on or in the legs. In some examples, the electrodes are configured as needles. Needle electrodes may be disposed within a cavity in a leg. Needle electrodes may initially be disposed within a leg(s) and then extended outward of the leg(s). Needle electrodes may be "pushed" out of the leg(s) in any suitable way, including, but not limited to, push/pull wires, slide blocks, and inflatable balloons. For example, the needle electrodes may be pushed out of the leg(s) by inflating a balloon (not shown) disposed within the leg(s). The needle electrodes may be capable of delivering Botox or other neurotoxins to the target tissue. Additionally or alternatively, the needle electrodes may be capable of delivering a cooling substance such as saline, to prevent the tissue immediately adjacent to the each needle electrode from over-heating and/or charring when energy is applied. For example, the needle electrodes may be connected to a tubing that would lead to a source of neurotoxins, cooling substances, and/or any other desired, infusible material. In some examples, needle electrodes may deliver bulking agents. The needle electrodes may have individual wiring connecting the electrodes to a device capable of delivering and/or measuring electrical energy, including, for example, controller 270.

Catheter 242 may be a tube made from any suitable biocompatible material known to one of ordinary skilled in the art having sufficient flexibility to traverse a patient's body, including a urinary tract. Such materials may include, but are not limited to, rubber, silicone, silicone rubber, synthetic plastics, and/or polymers, such as a polyolefin triblock polymer like poly(Styrene-block-IsoButylene-block-styrene)(SIBS), latex, polyurethane, polytetrafluoroethylene (PTFE), ethylene tetrafluoroethylene (ETFE), perfluoroalkoxy (PFA), polyether ether ketone (PEEK), high density polyethylene (HDPE), and/or polypropylene (PP). In another example, the material forming catheter 242 may be a superelastic material such as nitinol, which is a nickel-titanium alloy. In yet another example, catheter 242 may include one or more metals and/or alloys.

Catheter 242 may have any cross-sectional shape and/or configuration and may be any desired dimension that can be received in the desired aspect of the patient's body, including the lower urinary tract. An outer sheath (not shown) may surround catheter 242. The outer sheath may be constructed from an insulating polymer material such as polyamide, polyurethane, or any other suitable material. At least a portion of the outer sheath, such as a distal portion, may be deflectable and/or steerable. Catheter 242 may also include one or more lumens extending from proximal end 238 of the catheter 242 to distal end 230 of the catheter 242. The lumens may have any size, cross-sectional area, shape, and/or configuration.

In one example, medical device 250 may attach to or may include a computer system including a controller 270 and/or an interface 280. Controller 270 may include signal processing and/or an electrical energy source in or connected to handle 234 of medical device 250 via wires 260 and wires 266, respectively. In some implementations, medical device 250 may include other components, including, but not limited to, a fluid source, a coolant source, and/or a laser source.

Controller 270 may control and/or allow an operator to control the operation of various components of medical device 250. In some implementations, controller 270 may include, for example and without limitation, a processor and memory. The memory may include any type of random access memory (RAM) or read-only memory (ROM) embodied in a physical storage medium, such as magnetic storage including floppy disk, hard disk, or magnetic tape; semiconductor storage such as solid state disk (SSD) or flash memory; optical disc storage; cloud storage; Digital Imaging and Communications in Medicine (DICOM) compatible storage; or magneto-optical disc storage. Software may include one or more applications and an operating system. According to one aspect, the memory may store processor-readable instructions, such as instructions for evaluating electrical signals. The processor may execute those instructions to perform one or more method steps. The processor may, for example, instruct the electrical energy source to activate.

In some implementations, controller 270 (or the processor within controller 270) may control the frequency, pattern, and destination of electrical energy from the electrical energy supply to one or more of electrodes 1-20. Controller 270 (or the processor within controller 270) may receive and/or process electrical signals received from medical device 250, including from electrode array 116 and/or any of electrodes 1-20. Controller 270 (or the processor within controller 270) may also perform a variety of tasks depending on the nature of medical device 250 such as determining the geometrical characteristics of a region of interest, generating images of the region of interest and/or graphical representations of received electrical signals for output to a display, e.g., interface 280, or controlling the delivery of therapy to the target site(s). Controller 270 (or the processor within controller 270) may communicate with interface 280. Such communication may include information related to received signals and/or processed signals.

In some implementations, controller 270 (or the processor within controller 270) may be connected to interface 280. The interface 280 may communicate to controller 270 (or the processor within controller 270) input commands from an operator, including commands used to control and/or provide data to an energy supply source, electrodes, and/or any other components of medical device 250. Interface 280 may include user input device(s), including but not limited to any type or combination of input/output devices, such as a display monitor, touchpad, touchscreen, microphone, camera, keyboard, wearable device (watch, band, earphone, etc.), and/or mouse. In some examples, interface 280 and controller 270 may be a single unit, for example, a tablet, a smartphone, and/or a personal computer. Interface 280 may include a display screen for output to an operator. The display screen may display, for example, graphical representations of electrical signals received from one or more of electrodes 1-20 (e.g., FIGS. 3A and 3B), communicated to and processed by controller 270 (or the processor within controller 270). Additionally or alternatively, a virtual map of the organ or tract to-be analyzed and/or treated may be displayed, for example, on a display screen of interface 280. FIGS. 2A-2E illustrate an exemplary display of a virtual bladder 202 in examples where the to-be analyzed body part is a bladder.

Exemplary Methods of Use

In some implementations, the analyzed and/or treated interior wall of the patient may be any organ or body tract of a patient's body, including, the bladder, intestines, the urinary tract, and/or the digestive tract. For example, catheter 242 with electrode array 116 may be inserted into a patient. In examples where the analyzed and treated interior wall is the bladder, electrode array 116 may be inserted into the body through the urethra to the bladder in a contracted configuration (not shown). For example, in the contracted configuration, electrode array 116 may be located within a lumen of catheter 242 during insertion and then deployed out of the distal end 230 of catheter 242 and open to an expanded configuration (as shown in FIG. 1) once the distal end 230 is in the desired position within the bladder (or other desired organ). In some examples, electrode array 116 may be fixed on the distal end of the elongate member. The elongate member may be moveably disposed within the lumen of the catheter 242. In some example electrode array 116 may include sensors such as pressure sensors, biochemical sensors, pH, potassium, sodium, and similar sensors. These sensors may aid in determining bladder wall abnormality (in addition to impedance/myogenic activity electrodes).

As previously mentioned, in some examples, a virtual map of a desired body part may be generated, e.g., by a processor within controller 270, and displayed, e.g., on interface 280. In some examples, the displayed virtual map may be pre-set. For example, interface 280 will display the same body part with the same shape and the number and configuration of electrodes during every use/procedure. In other examples, the displayed virtual map may be based on real-time data/analysis. For example, data analysis may involve pattern recognition in which a particular pattern is recognized as a signature of bladder activity. Each time an electrode senses this pattern (e.g., by finding a match in a previously recorded database of responses/patterns), the active area may be identified/marked. For example, information may be stored on medical device 250, so that, once medical device 250 is connected to controller 270 and/or interface 280, the virtual map may be generated based on the shape of the electrode array, number of electrodes, and/or electrode configuration. Similarly, controller 270 and/or the processor within controller 270 may be able to sense the shape of the electrodes so that, once in an expanded configuration (e.g., contracting an interior wall of a body part), the shape of the electrode array may affect the displayed shape of the body part. For example, electrode array 116 may expand to contact the interior walls of the bladder and based on the expanded shape of electrode array 116, a virtual map may be generated that approximates the size and shape of the patient's bladder.

Figure 2A:
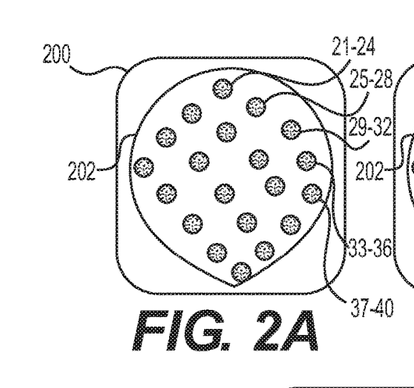
FIGS. 2A-E illustrate exemplary virtual bladder maps output in accordance with principles of the present disclosure.

FIG. 2A illustrates an exemplary virtual map of a bladder, after inserting and expanding an electrode array and prior to the electrodes engaging an interior wall of the bladder (as explained further below). As shown in FIG. 2A, each electrode (e.g., electrodes 1-20 of FIG. 1) is represented by a circle (e.g., representative markings 21-40), but the virtual maps of the present disclosure are not limited thereto. For example, electrodes may be represented by numbers, letter, other shapes, etc. Further, each representative marking may represent more than one electrode, for example, each marking may represent an electrode pair. Each representative marking (e.g., each circle of FIGS. 2A-E) for the electrodes in the virtual map may have an indicia indicating that electrodes status. The indicia may be a variety of shading, colors, symbols, letters, numbers, etc. The electrodes may have and/or the processor of controller 270 may detect any number of electrode statuses. In the examples, shown in FIGS. 2A-E, the electrodes have four statuses; not engaged, engaged, needs treatments, and effectively treated. These statuses may be indicated by displaying the representative markings in four different colors, e.g., yellow, green, red, and blue, respectively. In some examples, the statuses may be indicators (off, on, ready, complete, etc.), numbers (e.g., 1, 2, 3, 4, etc.), letters (e.g., A, B, C, D, etc.), or symbols (e.g., ≈, ±, −, +, or stop sign, or thumbs up, sad face, smiley face, etc.). FIG. 2A illustrates a virtual bladder map when none of the electrodes are engaged with patient tissue and/or the processor within controller 270 has not detected engagement of the electrodes with tissue. The lack of engagement of each of the representative markings (e.g., circles) is indicated by a first shading or a first color (e.g., yellow). All of the representative markings in FIG. 2A are a first shading/color, indicating that none of the electrodes have been engaged with patient tissue (e.g., an interior wall of the patient's bladder).

Figures 2B, 2C:
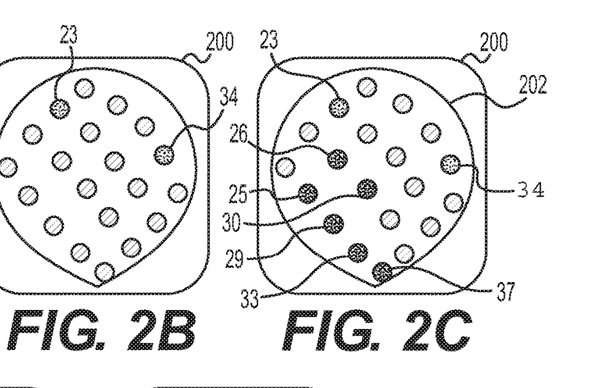

Once catheter 242 with electrode array 116 is introduced into the desired organ or tract the electrodes may engage with an interior wall (e.g., a wall of the bladder). For example, once in the desired position, electrode array 116 may transition to an expanded configuration and the electrodes engage with an interior wall (e.g., a wall of the bladder). In some implementations, a balloon (not shown) may be inflated within electrode array 116 to expand it. Alternatively, aspects of the electrode array may include memory-shape material, such as nitinol, to transition electrode array 116 to the expanded configuration. The created and/or displayed virtual map may then indicate that the electrodes have engaged the patient tissue. For example, FIG. 2B illustrates an exemplary virtual map of a patient's bladder once at least some of the electrodes have engaged an interior wall of the patient's bladder. Any engaged electrodes (or engaged electrode pairs) may be indicated by the representative marking (e.g., circle) being displayed with a second indicia. For example, the second indicia may be a second shading or a second color (e.g., green). In the example shown in FIG. 2B, not all of the electrodes (or electrode pairs) have engaged (or have been detected as engaged by the processor of controller 270). As shown in FIG. 2B, representative markings 23 and 34 remain displayed in the first shading/color, thus indicating that the associated electrodes have not engaged with the patient's tissue.

Once the electrodes have engaged with the interior wall of the patient and/or an operator determines that a sufficient number of representative markings have been displayed with the second indicia, the method may proceed to the next step, e.g., measuring electrical activity. As previously mentioned, electrical activity may be measured in any way, including measuring (1) spontaneous electrical activity, (2) vector impedance, and/or (3) resulting activity from paced electrode pairs.

I. Measuring Spontaneous Electrical Activity

Figure 3A:
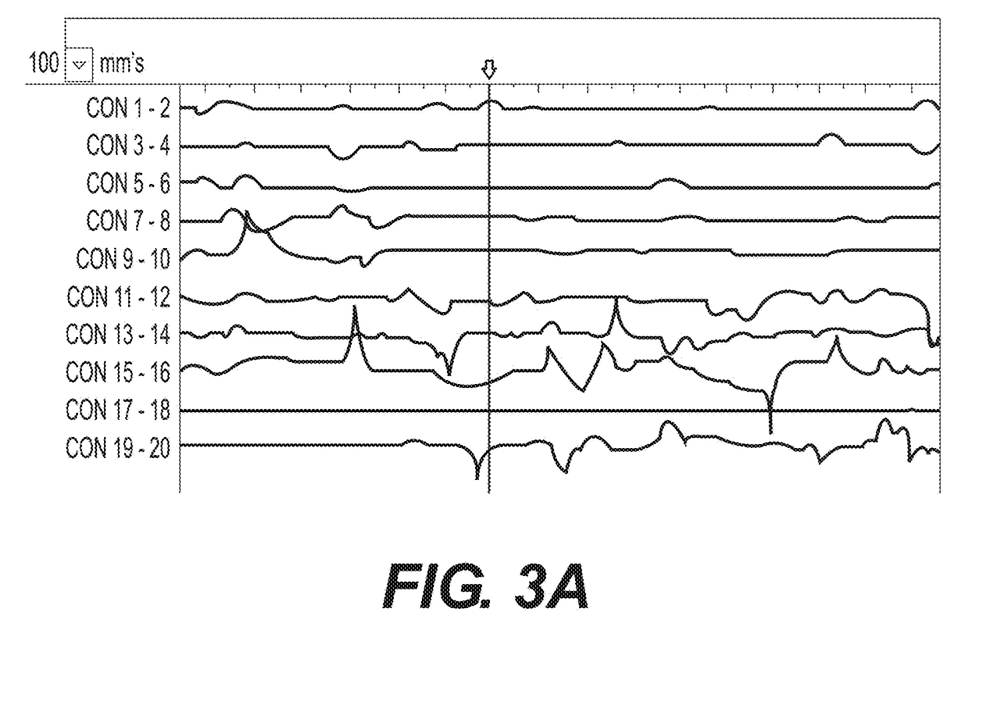
FIGS. 3A and 3B are graphical representations of electrical activity illustrating exemplary outputs to an interface in accordance with principles of the present disclosure.

In some examples, one or more of the electrodes may be used to measure spontaneous muscle activity at multiple sites (e.g., sites in which the electrodes engage the interior wall). Spontaneous electrical activity may be measured for between approximately one minute and approximately five minutes. In the example illustrated in FIG. 1, electrode array 116 may include electrodes 1-20. In some examples, measurements may be performed between adjacent electrode pairs (e.g., 1-2, 3-4, etc.). In other examples, measurements may be performed between non-adjacent electrode pairs. The measurements may be performed simultaneously at all electrode pairs or the measurements can be conducted at different times. To ensure measurements of electrical activity are not a product of a motion, physiological (e.g., myogenic) or extraphysiological (e.g., instrumentation, external noise, adequate grounding, etc.) artifact, each electrode measurement may be performed at normal and opposite polarity. Additionally or alternatively, one or more filters may be used to enhance the accuracy of the measurements by filtering out the artifact(s). For example, a mapping algorithm may be used, e.g., stored and processed in the memory and/or processor of controller 270. The mapping algorithm may filter out artifacts (e.g., heartbeat signals picked up by electrodes). For example, the mapping algorithm may identify signals observed at a consistent frequency and/or calculate the distance between peaks. If the distance between peaks for a particular electrode coincides with the patient's heartbeat and/or known/common human heartbeats, or breathing patterns, the data from that electrode may not be analyzed and/or may be filtered out. In some examples, the electrode may be turned off. An operator may change the sensitivity of the filter, as necessary, to either increase or decrease sensitivity to the signal and filter out noise or pick up a smaller signal. The sensitivity of the filter may need to be adjusted for patients with pacemakers. For example, pacing impulses may introduce about 0.5 ms pacing artifact signals. A strong RF current and/or high pacing current may disrupt normal pacemaker activity. This may cause unwanted arrhythmias and/or other risks to patient with an implanted pacemaker Electrodes may measure electrical activity and communicate resulting electrical signals to a processor (e.g., the processor within controller 270). In some examples, the processor within controller 270 may process these electrical signals and/or output the signals for display at interface 280. FIG. 3A illustrates a graphical representation of electrical activity. FIG. 3A illustrates an exemplary output of spontaneous electrical activity measured by electrode array 116 of FIG. 1 and/or displayed at interface 280 of FIG. 1. Spontaneous activity is smooth muscle contraction indicated by myopotentials recorded from the electrode array. Spontaneous activity could also be nerve potentials, also recorded from the electrode array. Impedance is current injected between two electrodes and the corresponding voltage measured. Impedance may be used to determine whether or not the electrodes are contacting tissue and also changes in the relative volume or distance between electrodes. As a result, an electrode array (e.g., electrode array 116) may sense local electrical myopotentials and then detect any corresponding mechanical contractions of the bladder through the use of impedance. Mechanical contractions may be local involving a small area of the bladder indicated by fewer corresponding electrodes, or more global involving the entire bladder indicated by changes to most or all electrodes on the array.

Once spontaneous electrical activity is measured, one or more of the electrodes that measured a highest relative electrical activity may be determined. The highest relative electrical activity may be calculated by determining the cumulative current intensity over time. For example, the operator may review the measured electrical activity (e.g., by reviewing graphical representations of electrical activity like FIG. 3A) and/or a processor (e.g., the processor in controller 270) may determine the electrode(s) and/or electrode pair(s) with the highest relative electrical activity. In the example illustrated in FIG. 3A, electrical activity measured between electrode pair 9-10; electrode pair 15-16; and electrical electrode pair 19-20 may be determined to be the highest electrical activity. In some examples, once the determination of which electrode(s) measure the highest relative electrical activity (by the operator reviewing representation of the electrical activity and/or by the processor) is made, the virtual map 200 may display the representative markings associated with these electrodes (e.g., representative markings associated with electrodes 9, 10, 15, 16, 19, and 20) with a third indicia. As shown in FIG. 2C, electrodes 9, 10, 15, 16, 19, and 20 are represented by markings 25, 26, 29, 30, 33, and 37 and thus, these markings are displayed with a third indicia (e.g., red) in virtual map 200 of FIG. 2C and/or on interface 280 of FIG. 1. In some examples, instead of keeping those electrodes that do not measure a need for treatment (e.g., the remaining electrodes after markings 25, 26, 29, 30, 33, and 37 are displayed as the third indicia) as the second indicia, these remaining electrodes may be displayed with a fourth indicia to indicate they were measured and determined not in need of treatment. In some examples, once a high area of activity is identified, a different electrode array (for example, an electrode array with smaller spaces between electrodes) may be used to provide a denser map of the area. Additionally or alternatively, an electrode array may be moved to ensure the signals are correct (e.g., if the same map is obtained after moving the array, the abnormal spot may be confirmed.).

Figure 2D:
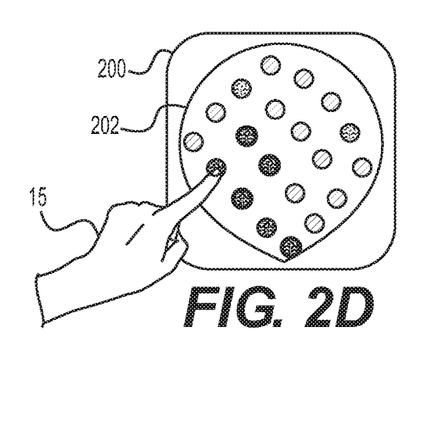
Figure 2E:
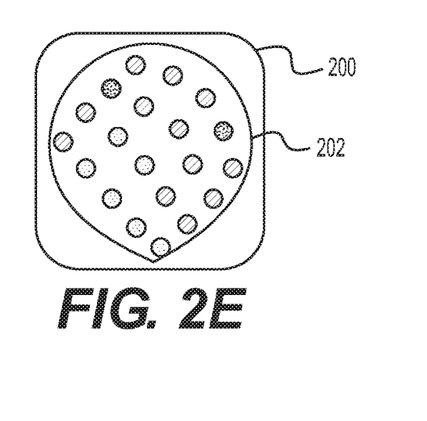

FIG. 2D illustrates an exemplary selection mechanism, e.g., an operator touching the desired representative marking on a touchscreen, for selecting sites for treatment. In some examples, sites that measure the highest relative spontaneous electrical activity, e.g., sites/representative markings displayed with the third indicia, are the sites identified for treatment. Thus, the operator may select markings 25, 26, 29, 30, 33, and 37 to treat the sites of tissue that are engaged with electrodes 9, 10, 15, 16, 19, and 20. Interface 280 may be a tablet or PC, touch screen, that allows the operator to select these and/or any desired sites for treatment. The applied treatment may be any known treatment, including applying radio frequency energy, ultrasound energy, laser energy, cryoablation, microwave ablation, a Botox injection, a neurolytic agent, optical energy, irreversible electroporation, a bladder resection, pacing, magnetics, ultrasound thermal treatment, hydrogel injection, injection of a material to create a physical or chemical barrier for signal transduction, or injection of any drug or drug-carrier combination formulation. A variety of methods of ablating are described in more detail below and may be used in combination with any of the ways of measuring electrical activity and/or any known treatment. In some examples, the utilized medical device only includes the capabilities to provide one form of treatment. In other examples, interface 280 of FIG. 1 and/or virtual map 200 of FIGS. 2A-E may provide the operator with the ability to select one or more forms of treatment for the selected treatment site(s).

Figure 3B:
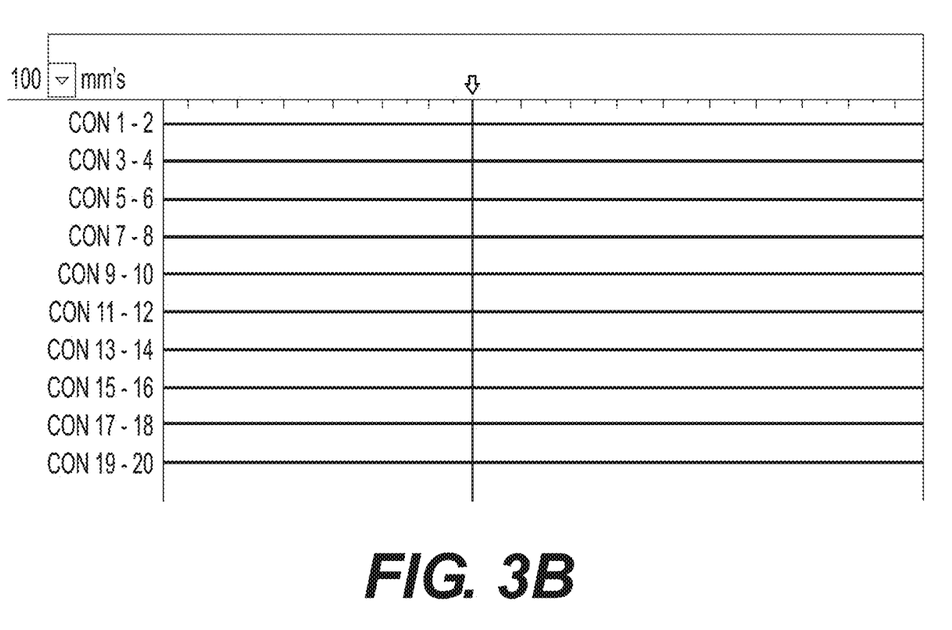

Once the selected treatment is complete, the electrical activity may be measured again, in any way, including measurement of spontaneous electrical activity. In some examples, a new virtual map may be generated. In some examples, virtual map 200 may be updated with the new measurements. The processor within controller 270 may process these electrical signals and/or output the signals for display at interface 280. FIG. 3B illustrates a graphical representation of electrical activity measured after "successful" or "effective" treatment. An effective treatment may be determined by the operator reviewing a graphical representation and determining that the variations in the lines are within a certain threshold (e.g., ±5%). In some examples, an operator may determine that the treatment was successful by determining that the lines are substantially horizontal lines, similar to those shown in FIG. 3B. In some examples, substantially horizontal lines may not be necessary to deem the treatment effective. For example, an operator may compare the pre-treatment electrical activity to the post treatment electrical activity (e.g., interface 280 may display FIGS. 3A-B side-by-side or one as an overlay over the other). The treatment may be considered successful if the electrical activity is merely less than the pre-treatment activity. The graphical representation would illustrate decrease or reduced electrical activity by displaying flatter or more horizontal lines. In some examples, the processor within controller 270 may determine that the measured electrical activity is either lower than the threshold variance or lower than the pre-treatment level. In some examples, once the determination of which electrode(s) have successfully/sufficiently treated the corresponding site is made, the virtual map 200 may display the representative markings associated with the treated electrodes (e.g., representative markings associated with electrodes 9, 10, 15, 16, 19, and 20) that have been determined to be successfully treated with a fourth indicia. As shown in FIG. 3B, electrodes 9-10, 15-16, and 19-20 are now substantially horizontal lines and thus, an operator or a processor (e.g., the processor within controller 270) may determine that the treatment administered after the corresponding markings 25, 26, 29, 30, 33, and 37 were selected in FIG. 2D was successful/sufficient. Thus, these markings are displayed with the fourth indicia (e.g., blue) in virtual map 200 of FIG. 2E and/or on interface 280 of FIG. 1. Alternatively, once it is determined that treatment is successful, the representative markings may change to the second indicia (e.g., engaged, but not in need of treatment).

If, after treatment, the operator and/or processor determines the treatment was not sufficiently successful (e.g., the electrical activity has not sufficiently decreased and/or a representative marking is still displayed with the third indicia), the representative marking may be selected again (as shown FIG. 2D) and/or the same or different treatment may be applied to the site associated with the representative marking. In some cases, after treatment, sensors may measure a representative marking may be determined as "in need of treatment" that previously was not indicated as "in need of treatment" and/or was not previously displayed with the third indicia. The operator may select (see FIG. 2D), this electrode for treatment even if it was not treated the first time.

In some examples where the method of treatment includes ablation, the electrodes may be self-adjusting, e.g., "smart electrodes." As the ablation is applied, the electrodes and/or processor (e.g., the processor within controller 270) may continue to measure electrical activity. Once the electrical activity reaches a threshold level, ablation may be terminated.

II. Measuring Vector Impedance

In some examples, as an alternative to or in addition to spontaneous electrical activity, an impedance measurement may be made between each adjacent electrode pair (e.g., electrodes 1 and 2, 3 and 4, etc.). These measurements may be stored as "vector impedance" values. Once impedance values are measured and/or stored in controller 270 for each vector, a nerve recruitment curve may be acquired by titrating up the current for each of these vectors and measuring the EMG response at other electrodes. An activation threshold (e.g., the current at which an EMG response above a given threshold is measured) may be recorded and/or stored (e.g., in the memory of controller 270) for each vector. The activation threshold may be divided by the determined impedance for each vector (e.g., by the processor within controller 270) to determine the voltage required at each site. The operator and/or processor may determine the sites with lowest voltage required to elicit a response. In some examples, the representative markings associated with these sites in virtual map 200 may be displayed with the third indicator (e.g., markings 25, 26, 29, 30, 33, and 37 may be red). These sites may then be treated with any of the treatment methods described herein. For example, a user may select markings 25, 26, 29, 30, 33, and 37, as shown in FIG. 2D, and one of radio-frequency ("RF") energy, ultrasound energy (e.g., high intensity focused ultrasound), laser energy, cryoablation, microwave ablation, Botox injections, neurolytic agents, optical energy sources, irreversible electroporation, magnetics, ultrasound thermal treatment, hydrogel injection, injection of a material to create a physical or chemical barrier for signal transduction, or injection of any drug or drug-carrier combination formulation, and/or another suitable technologies that affect the reactivity of nerve may be applied to the sites determined to have lowest voltage required to elicit a response. As described above, it may be determined post-treatment whether treatment was effective and/or sufficiently successful. In some examples, both the electrical activity and any of the impendence vector calculations described above may be used as feedback after treatment to check that the treatment was effective.

III. Pacing Electrode Pairs

In some examples, as an alternative to or in addition to spontaneous electrical activity and/or impedance measurements, electrode pacing may be repeated at a given site (e.g., an electrode pair). First, as described above, a device (e.g., device 250 of FIG. 1) may be inserted into the body organ or tract of interest. Once the electrodes engage the tissue (e.g., as indicated by representative markings being displayed with a second indicia in FIG. 2B), electrical activity may be measured by pacing electrode pairs. For example, electrode pair 1-2 may be paced first and the resulting activity at other electrode pairs may be measured and stored. The electrode pairs may be paced at high and/or low frequency. For example, low frequency pacing may be approximately 0.5 Hz to approximately 10 Hz. According to one aspect, low frequency pacing may be approximately 2 Hz. In some implementations, high frequency pacing may be approximately 100 Hz to approximately 500 Hz and in some instances, approximately 300 Hz. In some examples, a lower frequency stimulation may target smooth muscle, while the higher frequency stimulation targets nerve tissue. In some examples, electrode pairs may be paced in a random order. Alternatively, electrode pairs may be paced in the same order every time, starting from one anatomical site to another anatomical site (e.g. from bladder neck to bladder dome, so the method always creates the map in the same way). After scanning mode is complete, an operator may view a graphical representation of electrical activity, similar to FIG. 3A, for each electrode pair. For example, interface 280 may display a first graphical representation of electrical activity when electrode pair 1-2 was paced, a second graphical representation of electrical activity when electrode pair 3-4 was paced, a third graphical representation of electrical activity when electrode pair 5-6 was paced, etc. The operator may compare these graphical representations to determine which electrode pair elicited (e.g., which graphical representation illustrated) the highest measured activity. In some examples, a processor (e.g., the processor within controller 270) may determine which electrode pairs elicited the highest measured activity at other, non-paced electrodes/sites. Once the electrode pairs eliciting the highest activity are identified, the representative markings associated with these pairs in virtual map 200 may be displayed with the third indicator (e.g., markings 25, 26, 29, 30, 33, and 37 may be red). These sites may then be treated with any of the treatment methods described herein. For example, a user may select markings 25, 26, 29, 30, 33, and 37, as shown in FIG. 2D, and one of radio-frequency ("RF") energy, ultrasound energy (e.g., high intensity focused ultrasound), laser energy, cryoablation, microwave ablation, Botox injections, neurolytic agents, optical energy sources, irreversible electroporation, magnetics, ultrasound thermal treatment, hydrogel injection, injection of a material to create a physical or chemical barrier for signal transduction, or injection of any drug or drug-carrier combination formulation, and/or another suitable technologies that affect the reactivity of nerve may be applied to the sites connected with electrode pairs that elicited the highest measured activity at other, non-paced electrodes/sites. As described above, it may be determined post-treatment whether treatment was effective and/or sufficiently successful. In some examples, both the electrical activity and pacing may be used as feedback after treatment to check that the treatment was effective.

Additional Exemplary Conditions and Methods

As mentioned above, ablation is one available form of treatment. In some example, the electrodes themselves (e.g., electrode 1-20 of electrode array 116) may be to utilized to ablate the tissue at or near the electrodes. In some examples, the electrodes may be positioned and ablated in ring or line or spiral conformation to disrupt nerve/muscle electrical signaling. In some examples, the ablation may be applied to nerves or muscles depending on the depth and anatomic location of the ablating electrodes (e.g. bladder dome and neck are ablated to affect nerves). For example, if major nerves are located at the sites of the ablating electrodes, the conditions (including depth) of ablation may be chosen so the ablation can be transmural and nerves near the bladder wall are ablated. In some examples, the ablation frequency may be selected to destroy nerves or selected to destroy muscle.

In some examples, the surface of the electrodes may be cooled, in order to penetrate deeper into the tissue. In some examples, the entire bladder may be cooled by circulating fluid to carry heat away. Additionally or alternatively, an open-irrigated device to cool tissue immediately adjacent to the electrodes may be included. Such a device may reduce charring and enable a larger lesion to be developed.

Ablation may denervate, but not have a significant, irreversible, or damaging effect on the tissue being treated, e.g., the inner surface of the bladder. For example, the application of mild ablation (e.g., ablation that does not cause mucosal surface disruption, transmural lesions, and/or smooth muscle layer perforation. may cause denervation in bladder wall, but, at the same time, maintain intact nerve function involved in bladder filling/emptying. For example, ablating tissue superficial to transmural in areas where there is no dense innervation may denervate while maintaining necessary nerve function. In another example, ablating superficially (or avoiding ablation) in areas with dense innervation (e.g., the bladder neck) may maintain nerve function. In another example, modulating the general visceral afferent fibers may reduce sensory feedback sent to the central nervous system. Reduced sensory feedback may result in reduced hypersensitivity when the detrusor muscle is stretched, and/or may directly modulate the efferent motor nerves in locations of greater hyper-reactivity.

In some examples, the act of ablation may cause the electrode to disengage the tissue. In these cases, the electrode may not accurately measure post-treatment electrical activity. Therefore, prior to measuring post treatment electrical activity (e.g., before FIG. 2E), contact with the tissue should be tested and confirmed (e.g., FIG. 2B) and, if necessary, contact should be reestablished.

In some examples, there may be an interim "test ablation" period between the mapping (e.g., generating and/or displaying virtual map 200) and the ablation step (e.g., in examples where the selected treatment is a form of ablation). For example, a medical device (e.g., medical device 250 and/or electrode array 116) may stimulate nerves and/or sense electrical activity in order to map and determine ideal ablation zones, inject these ablation zones with a short-acting nerve block (e.g., Botox, Lidocaine, Bupivacaine, etc.), and leave at each ablation zone a marker (e.g., small amounts of injectable ink/die and/or a fluoro-marker that may bio-resorb over time). The medical device may then be removed from the patient's body. In some examples, during specified period of time, e.g., between approximately 12 hours and approximately 48 hours, the patient may be monitored to ensure no significant adverse effects occur, e.g., urinary retention or other issues commonly observed with treatment, e.g., common Botox side effects. If an operator (e.g., medical professional or physician) determines the results to be satisfactory, permanent ablation therapy may be performed, for example, by locating the original ablation zones where the short-acting nerve block was used. In some examples, the original ablation zones or sites of previous treatment may be identified with a fluorescence imaging including a light emitting diode (LED) to identify the injected fluorescence dye.

FIG. 4 illustrates an exemplary electrode array 470. Similar to electrode array 116 of FIG. 1, electrode array 470 may be moveably disposed within a catheter, e.g., catheter 442 or, as shown in FIG. 4, and at distal end 430 of catheter 442. Electrode array 470 includes eight legs (e.g., legs 41-48), and each leg includes a plurality of electrodes.

In some examples, FIG. 4 represents an alternative exemplary display (e.g., on interface 280 of FIG. 1) of a digital version of electrode array 470. In such examples, after measuring the electrical activity (in any way described herein or known in the art) and determining the sites for treatment (in any way described herein or known in the art), representative markings (e.g., target icons at electrodes 480, 482, 484, and 486), may be displayed on an image of electrode array 470 to indicate to an operator which electrodes (1) measure the highest spontaneous electrical activity, (2) require the lowest voltage required to elicit a response, (3) when paced, elicit the greatest response in other electrodes, and/or (4) any other indicator of the need for treatment to the connected/engaged tissue site.

In some implementations, the ablation (or other treatment) may not be performed on the single electrode (or single electrode pair) indicated as needing treatment (e.g., those displayed as the third indicator, red), but instead on an entire leg of the electrode array. As shown in FIG. 4, four electrodes have been indicated with identifiers 480, 482, 484, and 486. Identifiers 480, 482, 484, and 486 are displayed as target icons in FIG. 4, but are not limited thereto. For examples, identifiers 480, 482, 484, and 486 may be any indicia, including, colors, shapes, shading, etc. Three of these are on leg 41. In this example, treatment may be provided over the entire leg (not just the electrodes indicated for treatment), because it is the leg which has the highest activity. The treating/ablating in a vertical line in the bladder may result in reduction of electrical conduction around the bladder.

In some examples, the device may have four legs or "spline" for ablation. The four splines may be 90 degrees apart, thus dividing or separating the bladder into four sections. This may result in a reduction in signaling.

In some examples, multiple splines or legs may simultaneously provide treatment. In examples where the electrodes for treatment are concentrated in one section of the leg/spline, ablation may be performed on a partial length of the spline (but more than just the electrodes indicated for treatment).

A device (e.g., medical device 250) may additionally provide visualization during any of the methods or procedures described herein. This may provide an operator the ability to see the tissue, body organ, body tract, etc. being analyzed and treated. For example, visualizing the vasculature may assist an operator in avoiding the vasculature during ablation. Visualization may be provided via a working channel with a catheter (e.g., catheter 242 of FIG. 1). The working channel may be between approximately 24 Fr to approximately 25 Fr. In some examples, visualization may be provided via an ultrasound.

In one example, a method may include measurement of the entire bladder activity, then a 'rest phase' (e.g., no measurement), followed by another whole bladder measurement, followed by 'rest phase' and so forth. This way the bladder is mapped in different stages and a comprehensive map is created (using an average of activity per electrode for example) to pinpoint the highly active sites. The rest phase may include filling the bladder and/or stimulating (mechanical, electrical, etc.) the bladder, followed by another measurement and subsequent measurement-stimulus cycles from which an average may be obtained for a final bladder activity map.

In addition, aspects of the aforementioned embodiments and examples may be combined with any other aspects of any other embodiments or examples, without departing from the scope of the disclosure. Other embodiments of the present disclosure will be apparent to those skilled in the art from consideration of the specification and practice of the embodiments disclosed herein. It is intended that the specification and examples be considered as exemplary only, with a true scope and spirit of the disclosure being indicated by the following claims.

What is claimed is:

1. A treatment system comprising:
   a plurality of electrodes;
   a display;
   a memory device configured to store instructions for evaluating electrical signals; and
   a processor configured to execute the instructions to perform a method including:
      communicating to the display a virtual map including a representative marking with a first indicia for each electrode of the plurality of electrodes;
      determining which of the plurality of electrodes are in contact with internal tissue of at least one of a bladder, intestine, urinary tract and digestive tract;
      communicating to the display to change the representative marking from the first indicia to a second indicia for each electrode of the plurality of electrodes determined to be in contact with the internal tissue;
      measuring spontaneous electrical activity at each electrode of the plurality of electrodes in contact with the internal tissue;
      determining at least one electrode of the plurality of electrodes in contact with the internal tissue for treatment based on the measured spontaneous electrical activity; and
      communicating to the display to change the representative marking for the at least one electrode determined for treatment from the second indicia to a third indicia.

2. The treatment system of claim 1, wherein the method further includes: receiving, from the display, a selection of at least one electrode of the plurality of electrodes to apply treatment.

3. The treatment system of claim 1, wherein the method further includes: instructing the treatment system to apply treatment to the internal tissue in contact with the at least one electrode determined for treatment.

4. The treatment system of claim 3, wherein the treatment includes at least one of radio frequency energy, ultrasound energy, laser energy, cryoablation, microwave ablation, a Botox injection, a neurolytic agent, optical energy, irreversible electroporation, magnetics, ultrasound thermal treatment, hydrogel injection, injection of a material to create a physical or chemical barrier for signal transduction, or injection of any drug or drug-carrier combination formulation.

5. The treatment system of claim 3, wherein the method further includes: after instructing the treatment system to apply treatment to the internal tissue, measuring spontaneous electrical activity at each electrode of the plurality of electrodes in contact with the internal tissue.

6. The treatment system of claim 5, wherein the method further includes: determining at least one electrode of the at least one electrode determined for treatment for no treatment.

7. The treatment system of claim 6, wherein the method further includes: communicating to the display to change the representative marking for the at least one electrode used to apply treatment as a fourth indicia.

8. The treatment system of claim 5, wherein the method further includes: determining at least one electrode of the at least one electrode used to apply treatment for further treatment; and instructing the treatment system to apply further treatment to the internal tissue in contact with the determined at least one electrode.

9. The treatment system of claim 1, wherein the measuring spontaneous electrical activity includes at least one of measuring nerve potentials or myopotentials.

10. The treatment system of claim 1, wherein the method further includes: generating a graphical representation of the measured spontaneous electrical activity at each electrode of the plurality of electrodes in contact with the internal tissue.

11. The treatment system of claim 10, wherein the method further includes: communicating to the display the measured spontaneous electrical activity at each electrode of the plurality of electrodes in contact with the internal tissue.

12. The treatment system of claim 1, wherein the plurality of electrodes are disposed on a plurality of legs.

13. The treatment system of claim 12, wherein the method further includes: identifying a leg of the plurality of legs including at least two electrodes determined for treatment.

14. The treatment system of claim 13, wherein the method further includes: instructing the treatment system to apply treatment to the internal tissue in contact with each electrode disposed on the identified leg.

15. A method, comprising:
generating a virtual map of a plurality of electrodes, wherein each electrode of the plurality of electrodes is displayed with a first indicia;
engaging one or more of the plurality of electrodes with an interior wall of the patient at a plurality of locations of at least one of a bladder, intestines, urinary tract and digestive tract;
displaying each electrode of the plurality of electrodes engaged with the interior wall with a second indicia;
measuring spontaneous electrical activity at each electrode of the plurality of electrodes engaged with the interior wall;
identifying at least one electrode of the plurality of electrodes engaged with the interior wall for treatment based on the measured spontaneous electrical activity; and
displaying, prior to applying a treatment, the at least one electrode identified for treatment with a third indicia.

16. The method of claim 15, further comprising:
selecting at least one electrode of the plurality of electrodes for treatment; and applying treatment to the selected at least one electrode.

17. The method of claim 16, further comprising: after applying treatment, measuring spontaneous electrical activity at each electrode of the plurality of electrodes engaged with the interior wall.

* * * * *